United States Patent [19]
Ericsson et al.

[11] Patent Number: 5,101,051
[45] Date of Patent: Mar. 31, 1992

[54] PROCESS FOR THE PRODUCTION OF EPOXIDES

[75] Inventors: Harriet Ericsson, Göteborg; Elina Sandberg, Ödsmål; Eva Gottberg-Klingskog, Västra Frölunda, all of Sweden

[73] Assignee: Eka Nobel, Bohus, Sweden

[21] Appl. No.: 694,496

[22] Filed: May 2, 1991

[30] Foreign Application Priority Data

Jun. 13, 1990 [SE] Sweden ............................. 9002107

[51] Int. Cl.$^5$ ............................. C07D 301/14
[52] U.S. Cl. ............................. 549/525; 260/413; 562/6; 562/590
[58] Field of Search ......................... 549/525

[56] References Cited

U.S. PATENT DOCUMENTS

| 2,347,434 | 4/1944 | Reichert et al. | 549/525 |
|---|---|---|---|
| 2,377,038 | 5/1945 | Reichert et al. | 549/525 |
| 3,141,896 | 7/1964 | Stein et al. | 549/525 |
| 3,284,419 | 11/1966 | Helffench | 549/525 |
| 4,243,599 | 1/1981 | Irogai et al. | 549/525 |
| 4,391,753 | 7/1983 | Hardy et al. | 549/525 |
| 4,647,678 | 3/1987 | Eckwert et al. | 549/525 |

FOREIGN PATENT DOCUMENTS

| 687184 | 5/1964 | Canada | 549/525 |
|---|---|---|---|
| 1015782 | 9/1957 | Fed. Rep. of Germany | 549/525 |
| 108374 | 5/1964 | Netherlands | 549/525 |
| 1048318 | 11/1966 | United Kingdom | 549/525 |

*Primary Examiner*—J. E. Evans
*Attorney, Agent, or Firm*—Fred Philpitt

[57] ABSTRACT

Epoxides are prepared by reaction of compounds containing olefinic unsaturation, for example α-olefins, terpenes and steroids, with an aliphatic diperoxydicarboxylic acid. The diperoxydicarboxylic acid contains 2 to 16 carbon atoms and suitably at least 6 carbon atoms. The process gives a good epoxidation process and does not give rise to byproduct formation.

7 Claims, No Drawings

PROCESS FOR THE PRODUCTION OF EPOXIDES

The present invention relates to a process for the production of epoxides by reaction of compounds containing olefinic unsaturation and a peroxycarboxylic acid and more particularly to such a process wherein solid diperoxydicarboxylic acids are used for epoxidation.

Epoxidation of compounds containing olefinic double bonds to oxiranes using peracids is a very well known reaction. For epoxidation with peracids, liquid water soluble monoperoxy carboxylic acids, such as performic acid, peracetic acid and perpropionic acid, are conventionally used. In practice, peracetic acid has predominantly been used. Certain solid peracids, such as monoperoxyphthalic acid, have also been used for epoxidation and this is for example disclosed in the U.S. Pat. No. 4590286. In order to get an epoxidation process which is both economically and technically satisfactory it is required that the carboxylic acid formed at the epoxidation, and optionally remaining percarboxylic acid, easily can be recirculated after the epoxidation so that percarboxylic acid can be regenerated and it is required that the epoxidation can be carried out efficiently and rapidly with different types of olefins and also that the obtained epoxide is as free from contaminating byproducts as possible. When monoperoxycarboxylic acids, such as peracetic acid, are used there are difficulties in getting a fully satisfactory separation of the formed carboxylic acid after the epoxidation in order to regenerate the peracid. Peroxycarboxylic acids such as peracetic acid also give problems with byproduct formation. In order to prepare peroxycarboxylic acids from carboxylic acids it is necessary to use a strong acid, such as sulfuric acid or methanesulfonic acid, as a catalyst. If there are residues present at the epoxidation this leads to ring-opening of the epoxide and formation of byproducts such as diols and esters. Special measures must thus be taken in order to avoid these problems. Hereby attempts have mainly been made to add different bases in order to neutralize the acid. In addition to consumption of additional chemicals this method also leads to problems at the recirculation and working up of the carboxylic acid which is regenerated at the epoxidation. For solid peracids such as monoperoxyphthalic acid the byproduct problems are not as great since a solid product can easily be purified. However, these solid peroxycarboxylic acids have disadvantages as concerns recirculation/regeneration since they cannot be generated directly from the carboxylic acid and hydrogen peroxide. They require preparation from the anhydride or the ester of the carboxylic acid and consequently an additional step.

According to the present invention it has been found that a very satisfactory epoxidation process can be obtained by utilization of solid aliphatic diperoxydicarboxylic acids for the epoxidation. The above described problems are avoided when diperoxydicarboxylic acids are used. Since the diperoxydicarboxylic acids are solid, remaining residues of acid can easily be removed by filtration and washing of the produced diperoxydicarboxylic acid and problems with byproducts are hereby essentially suppressed. After the epoxidation reaction the dicarboxylic acids are precipitated and can thus easily be separated for regeneration of the diperoxydicarboxylic acids. It has also been found that the solid aliphatic diperoxydicarboxylic acids which are used according to the invention give a very rapid and efficient epoxidation of c-olefins. The problems at epoxidation with for example peracetic acid are most severe for these olefins, since they are epoxidised more slowly than internal olefins and thus the byproduct formation is high.

The present invention thus relates to a process for the production of epoxides by reaction of compounds containing olefinic unsaturation with aliphatic diperoxydicarboxylic acids as defined in the patent claims.

The diperoxydicarboxylic acids which are used are characterized by the general formula

$$HOOOC(CH_2)_nCOOOH$$

wherein n is an integer of from 0 to 16. These dipoeroxydicarboxylic acids are solid, and hereby is understood that they are solid at room temperature, about 20° C. The diperoxydicarboxylic acids of the given formula are per se known and prepared in conventional manner, for example by oxidation of the corresponding carboxylic acid with hydrogen peroxide in the presence of a strong acid, such as sulfuric acid or methanesulfonic acid. As examples of diperoxydicarboxylic acids for epoxidation according to the present process can be mentioned diperoxyoxalic acid, diperoxysuccinic acid, diperoxyadipic acid, diperoxypimelic acid, diperoxysuberic acid, diperoxyazelaic acid, diperoxysebacic acid, diperoxybrassylic acid, diperoxydodecane dioic acid, diperoxytetradecane dioic acid. Diperoxydicarboxylic acids having totally at least 6 carbon atoms are preferred since they have a low solubility in water which means that the isolation after the epoxidation is facilitated. The diperoxydicarboxylic acids with lower number of carbon atoms are somewhat soluble in water and thus the separation work at the peroxidation is made more difficult. Further, the diperoxydicarboxylic acids with totally 6 to 18 carbon atoms are preferred since they have a lower content of active oxygen per weight unit which gives reduced risk of explosion and safer handling and use. The diperoxydicarboxylic acids with a total number of carbon atoms of from 6 to 12, ie n in the above given formula is 4 to 10, are particularly suitable. Especially preferred diperoxydicarboxylic acids are diperoxyadipic acid, diperoxysebacic acid and diperoxydodecane dioic acid, and particularly the last mentioned acid. In order to increase the safety at handling of the diperoxydicarboxylic acids and to diminish the risks of thermal decomposition it can be suitable to use for peroxy acids per se known stabilizers. Thus, for example, dipicolinic acid and phosphonic acids etc. can be used for stabilization. Suitable amounts of dipicolinic acid may be from about 100 to about 500 ppm, based on the total weight of the reaction mixture. In order to get the overall best safety in a working process with epoxidation and regeneration of diperoxydicarboxylic acid it is preferred that the oxidation of the carboxylic acids is carried out using methanesulfonic acid as catalyst since the raise in temperature hereby will be smaller than when sulfuric acid is used. Further, at preparation, handling and use of the diperoxydicarboxylic acids it can be suitable to dilute these with inert materials such as for example boric acid or siliceous flux, which neither influence the reaction rate nor the yields at the peroxidation and the epoxidation.

The olefinically unsaturated compounds which can be epoxidized according to the present invention are primarily aliphatic, straight or branched, olefins with one or several double bonds in internal or terminal position and having chain lengths from 3 to about 30 carbon atoms. As examples of such olefins can be mentioned propene, butene, pentene, isoamylene, hexene, hexadiene, octene, nonene, decene, dodecene, tetradecene. Alicyclic mono- or diolefins such as cyclohexene and cyclooctadiene can also be epoxidized according to the present process. The olefinically unsaturated compounds can further be terpenes such as limonene and pinene and also steroids such as cholesterol. It is not necessary that the compounds contain solely carbon and hydrogen but they can also contain functional groups as long as these do not interfere with the epoxidation or otherwise have a negative influence on the process. The olefinic compounds can thus also for example be unsaturated alcohols, esters and acids such as unsaturated fatty alcohols, fatty acids and fatty esters. The present process is particulary suitable for epoxidation of α-olefins having from 4 to 18 carbon atoms and especially for those having from 6 to 18 carbon atoms.

The reaction times and temperatures used at epoxidation according to the present process are primarily dependent on the reactivity of the unsaturated compound. Normally epoxidation of α-olefins is carried out at temperatures of from about 40° C. to about 70° C. and during a time period of from about 2 to about 8 hours. For activated olefins a high conversion can be obtained within half an hour to two hours at temperatures of from about 20° to about 40° C. It is suitable to use diperoxydicarboxylic acid to compound containing olefinic unsaturation in amounts such that the ratio of peroxycarboxylic acid group to unsaturation is within the range of from 0.1:1 to 10:1, and preferably within the range from 0.9:1 to 2:1. The epoxidation reaction can be carried out at normal pressure or at pressures up to about 20 or up to about 40 bar, depending on the starting material. In certain cases the epoxidation can be carried out in the absence of solvent. However, organic solvents are usually used in order to dissolve the olefin, suspend and partly dissolve the diperoxydicarboxylic acid and to carry formed reaction heat away. The requirement for the solvent is that it must not react with the diperoxydicarboxylic acid. As examples of suitable types of solvents can be mentioned ethers, ester and chlorinated hydrocarbons. As examples of some specific suitable solvents can be mentioned tetrahydrofuran, ethyl acetate, propyl acetate and chloroform. At the production of epoxides the olefinic unsaturated compound can either first be dissolved in a smaller amount of solvent and the diperoxydicarboxylic acid then be added under agitation and cooling or, alternatively, the diperoxydicarboxylic acid can be suspended in the solvent and the olefinically unsaturated compound be added under agitation and cooling. The diperoxydicarboxylic acid is suitably added to the unsaturated compound. This is particularly important at the epoxidation of activated olefins. The reaction is carried out under agitation and, as usual at reactions of this type where much heat is generated, under temperature control by cooling. After completed reaction the regenerated dicarboxylic acid can be removed by filtration. Dissolved residues of the dicarboxylic acid and optionally remaining diperoxydicarboxylic acid can be washed away, for example with sodium carbonate solution. The diperoxydicarboxylic acid can subsequently be regenerated from the dicarboxylic acid.

The invention is further illustrated in the following examples which, however, are not intended to limit the same. Parts and per cent relate to parts by weight and per cent by weight respectively, unless otherwise stated.

EXAMPLE 1

Diperoxyadipic acid, diperoxysuberic acid and diperoxydodecane dioic acid were prepared according to the following: The corresponding dicarboxylic acid was dissolved/suspended in 5 equivalents of methanesulfonic acid under agitation. The mixture was cooled on an ice bath to about 10° C. 2 equivalents of hydrogen peroxide were added dropwise under temperature control, so that the temperature did not rise too rapidly and so that it did not exceed 25° C. When all hydrogen peroxide had been added the mixture was warmed to 30° C. for an hour and then cooled again on an ice bath. The diperoxydicarboxylic acid was filtered off, washed with ice-cold deionized water and dried at room temperature and atmospheric pressure. Yields of from 80 to 90% diperoxydicarboxylic acid were obtained.

EXAMPLE 2

8 862 g (0.050 moles) α-olefin C12/C14 were mixed with 7 mg dipicolinic acid and 2 ml chloroform in a 100 ml three-neck flask equipped with thermometer and reflux condenser. 9.936 g (0.030 moles) diperoxydodecane dioic acid (80%) were added under agitation. The reaction mixture was warmed to 60° C. After 4 hours reaction at 60° C. the reaction mixture was cooled to room temperature. The regenerated dodecane dioic acid was filtered off and washed with chloroform. The combined organic phases were washed with sodium carbonate solution to remove remaining diperoxydodecane dioic acid.

The organic phases were dried with sodium sulfate and evaporated. The yield was 9.42 g and of this 94 per cent were epoxide and remaining 6 per cent were unreacted olefin. No hydrolysis products could be detected with gas chromatography.

In the following table epoxidations of several olefins with different diperoxydicarboxylic acids under varying reaction conditions are shown.

| Di peracid (equiv. peracid group) | Olefin (mmole) | Solvent (ml) 5) | Dipicolinic acid (ppm) 1) | Temp. °C. | Time hours | Yield % 2) |
|---|---|---|---|---|---|---|
| Diperoxyadipic acid (1.1) | Nonene (80) 3) | EtOAc (10) | — | 30 | 2/4 | 93/97 |
| Diperoxydodecane dioic acid (1.2) | α-Olefin $C_{12}/C_{14}$ (50) 4) | PrOAc (1) | 400 | 55 | 4/6 | 94/96 |
| Diperoxydodecane dioic acid (1.2) | α-Olefin $C_{12}/C_{14}$ (300) | THF (50) | 200 | 65 | 4/6 | 92/95 |
| Diperoxydodecane dioic acid (1.2) | α-Olefin $C_{12}/C_{14}$ (50) | CHCl$_3$ (2) | 300 | 60 | 4/6 | 94/97 |
| Diperoxyadipic acid (2.0) | 1-Dodecene (8) | PrOAc (10) | — | 50 | 5 | 89 |

-continued

| Di peracid (equiv. peracid group) | Olefin (mmole) | Solvent (ml) 5) | Dipicolinic acid (ppm) 1) | Temp. °C. | Time hours | Yield % 2) |
|---|---|---|---|---|---|---|
| Diperoxydodecane dioic acid (2.0) | " | " | — | " | " | 90 |
| Diperoxyadipic acid (2.0) | 1-Hexadecene (8) | EtOAc (10) | — | 55 | 5 | 93 |
| Diperoxydodecane dioic acid (2.0) | " | " | — | " | " | 83 |
| Diperoxyadipic acid (1.0) | Cyclohexene (8) | THF (5) | — | 30 | 5 | 84 |
| Diperoxysuberic acid (1.0) | " | " | — | " | " | 82 |
| Diperoxydodecane dioic acid (1.0) | " | " | — | " | " | 83 |
| Diperoxyadipic acid (2.0) | 1-Tetradecene (4) | PrOAc (5) | — | 55 | 4 | 91 |
| Diperoxyadipic acid + boric acid (2.0) | " | " | — | 50 | " | 93 |
| Diperoxyadipic acid + silic. flux (2.0) | " | " | — | 50 | " | 95 |

1) Calculated on the total weight of the reaction mixture.
2) Olefin converted to epoxide. The results are measured by gaschromatography.
3) Commercial mixture of straight and branched internal mono-olefins with 9 carbon atoms.
4) Commercial mixture.
5) THF = Tetrahydrofuran, EtOAc = Ethyl acetate, PrOAc = Propyl acetate

We claim:

1. A process for the production of epoxides by reaction of compounds containing olefinic unsaturation with a peroxycarboxylic acid, characterized in that the peroxycarboxylic acid is a solid diperoxydicarboxylic acid having the general formula HOOOC(CH$_2$)$_n$COOOH wherein n is an integer of from 0 to 16.

2. A process according to claim 1, characterized in that n in the general formula is an integer of from 4 to 14.

3. A process according to claim 1, characterized in that the diperoxydicarboxylic acid is diperoxyadipic acid, diperoxysebacic acid or diperoxydodecane dioic acid.

4. A process according to claim 1, characterized in that the diperoxydicarboxylic acid is utilized in amounts to compound containing olefinic unsaturation corresponding to a ratio of peroxycarboxylic acid groups per unsaturation in the compound which is within the range of from 0.1:1 to 10:1.

5. A process according to claim 1, characterized in that the compound containing an olefinic unsaturation is an aliphatic mono- or diolefin having from 3 to 30 carbon atoms, an alicyclic mono- or diolefin, a terpene or a steroid.

6. A process according to claim 5, characterized in that the compound is an α-mono olefin having from 4 to 18 carbon atoms.

7. A process according to claim 1, characterized in that the reaction is carried out in the presence of dipicolinic acid.

* * * * *